United States Patent [19]
Campbell

[11] Patent Number: 5,884,775
[45] Date of Patent: Mar. 23, 1999

[54] SYSTEM AND METHOD OF INSPECTING PEEL-BEARING POTATO PIECES FOR DEFECTS

[75] Inventor: Duncan Campbell, Central Point, Oreg.

[73] Assignee: SRC Vision, Inc., Medford, Oreg.

[21] Appl. No.: 665,078

[22] Filed: Jun. 14, 1996

[51] Int. Cl.[6] ............................................... B07C 5/342
[52] U.S. Cl. .................... 209/581; 209/587; 209/938; 250/223 R; 250/341.8; 250/910; 356/407; 356/425
[58] Field of Search ................................. 209/552, 559, 209/563, 564, 576, 577, 579, 580, 581, 582, 587, 938, 939; 250/223 R, 910, 330, 341.8; 356/402, 407, 425

[56] References Cited

U.S. PATENT DOCUMENTS

| | | | |
|---|---|---|---|
| 3,675,769 | 7/1972 | Story | 209/73 |
| 3,773,172 | 11/1973 | McClure et al. | 209/73 |
| 4,168,005 | 9/1979 | Sandbank | 209/552 |
| 4,262,806 | 4/1981 | Drabs | 209/577 |
| 4,279,346 | 7/1981 | McClure et al. | 209/582 |
| 4,581,632 | 4/1986 | Davis et al. | 250/572 X |
| 4,634,881 | 1/1987 | Billion | 250/572 |
| 4,723,659 | 2/1988 | Billion | 209/576 |
| 4,738,175 | 4/1988 | Little et al. | 83/71 |
| 4,909,930 | 3/1990 | Cole | 209/587 X |
| 5,085,325 | 2/1992 | Jones et al. | 209/580 |
| 5,134,291 | 7/1992 | Ruhl, Jr. et al. | 250/341 |
| 5,141,110 | 8/1992 | Trischan et al. | 209/524 |
| 5,440,127 | 8/1995 | Squyres | 250/341.8 |
| 5,443,164 | 8/1995 | Walsh et al. | 209/580 |
| 5,464,981 | 11/1995 | Squyres et al. | 250/341.8 |
| 5,638,961 | 6/1997 | Satake et al. | 209/581 X |

FOREIGN PATENT DOCUMENTS

| | | | |
|---|---|---|---|
| 0247016 | 5/1987 | European Pat. Off. | |
| 2430272 | 2/1980 | France | |
| 2697450 | 5/1994 | France | 209/587 |
| 1301147 | 12/1989 | Japan | |

OTHER PUBLICATIONS

NC State University, *UV/VIA/NIR Measurement Fundamentals*, Appendix 1, "Theory of Near Infrared Reflectance Spectroscopy," 1992.

The Infrared Information Analysis Center, Environmental Research Institute of Michigan, *The Infrared andbook*, Revised Edition, pp. 3–13, 3–121, 3–129, 3–130, 1985.

*Primary Examiner*—Tuan N. Nguyen
*Attorney, Agent, or Firm*—Stoel Rives LLP

[57] ABSTRACT

A system and method of operation performing automated optical inspection to remove peel-bearing defective potato pieces from a random mixture of peel-bearing defective and acceptable potato pieces use near infrared light as a source of illumination. The system implements a method of illuminating the mixture with near infrared light, detecting light reflected by the potato pieces under inspection, identifying defective potato piece surface regions based on the detected reflections, and removing the defective items from the mixture. The system and method the system implements permit the inspection of peel bearing potato pieces for the presence of peel covered defects.

9 Claims, 3 Drawing Sheets

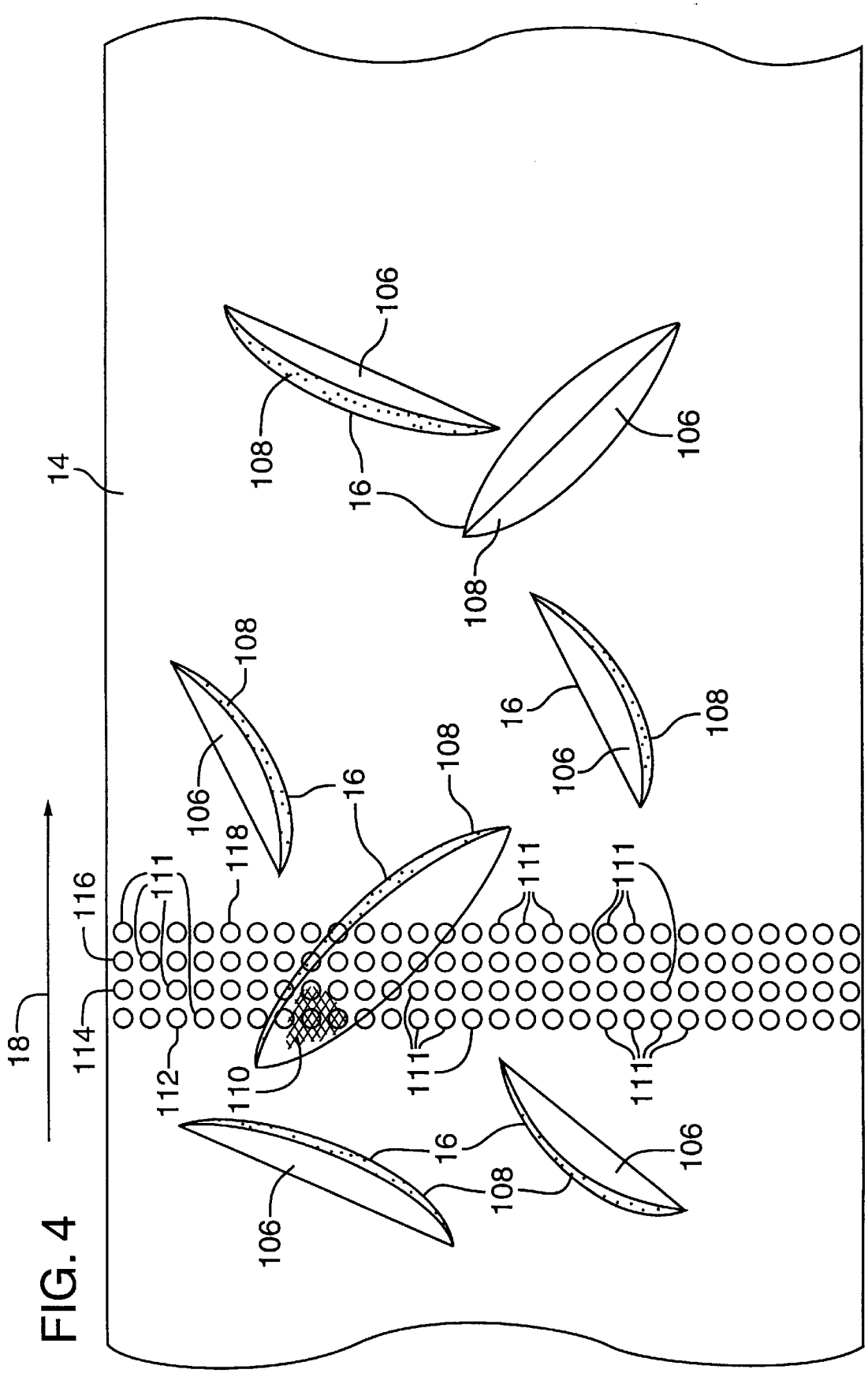

SYSTEM AND METHOD OF INSPECTING PEEL-BEARING POTATO PIECES FOR DEFECTS

TECHNICAL FIELD

The present invention pertains to automated optical inspection and sorting systems and methods and, in particular, to systems and methods for removing defective potato pieces from a random mixture of acceptable and defective peel-bearing potato pieces.

BACKGROUND OF THE INVENTION

Automated optical inspection and sorting systems have been used to inspect and sort various target specimens including fruits and vegetables, processed meat, baked goods, and other foodstuffs; to remove different types of recyclable material; and to sort foreign or defective items from supplies of wood chips. These systems typically employ video systems with charge-coupled device line scan cameras to acquire images of target specimens moved on a conveyor belt across an optical scanning area. Illumination of the specimens is generally provided by either broad-spectrum tubular fluorescent lamps or rare gas discharge lamps. Signal processing circuitry identifies variations in the shade of target specimen images and sorts target specimens accordingly.

Shipments of potato pieces, such as raw french fries, from producers often include defective pieces that may contain potato rot, potato eyes, or potato dark green flesh. It is desirable to remove such contaminants before shipping potato pieces to consumers or fast food outlets. The removal of defective pieces also helps to establish the actual quantity of acceptable pieces in a shipment.

Traditionally, consumers have preferred that potato pieces, such as french fries, be prepared from potatoes that had been peeled prior to being cut into pieces. Because of this preference, potato piece sorting systems built in the past have generally been configured to reject potato pieces bearing potato peel.

More recently, however, potato piece foods that are still peel bearing have surged in popularity. For example, peel-bearing french fries have become steadily more available and more accepted over the past several years. It is possible that consumers perceive these products to be more healthful and "natural" than their naked brethren.

Unfortunately, existing potato piece sorting systems are not very useful for removing peel-bearing defective potato pieces from a random mixture of defective and acceptable peel-bearing pieces because, as noted, such systems are configured to reject all peel-bearing pieces. Moreover, this inadequacy is not overcome by means of simple recalibration because current systems use broad band visible light, which makes it difficult to distinguish an otherwise acceptable peel-bearing potato piece region from a potato piece region that suffers from "potato eye," is blighted by potato rot, or is dark green. Moreover, because potato peel is substantially opaque to visible spectrum light, a covering of peel inhibits defect inspection of a portion of the potato flesh.

SUMMARY OF THE INVENTION

An object of the present invention is, therefore, to provide a system and method of automated optical inspection and sorting that distinguish peel-bearing defective potato pieces in a random mixture of defective and acceptable peel-bearing potato pieces.

Another object of the present invention is to provide such a system and method that can examine a peel-bearing potato piece for peel covered defects.

According to the present invention, a system and method of automated optical inspection and sorting utilize differences in reflectivity of near infrared light to distinguish between defective pieces and acceptable pieces of peel-bearing potato. In a preferred embodiment, a source of near infrared light illuminates a random mixture of peel-bearing potato pieces, identifies the defective pieces, and uses the identification to sort the defective pieces from the mixture.

Near infrared light has the advantage that it is reflected quite well by both peeled and peel-bearing potato. Furthermore, it is not reflected well by "potato eyes," potato rot, or potato dark green flesh. Therefore, it is generally fairly easy to distinguish good white potato flesh from defective potato flesh by illuminating the potato pieces with near infrared light. Moreover, potato peel is somewhat transparent to near infrared light; therefore, where a defective region is hidden beneath the peel, the infrared system may nevertheless identify the defective region.

Additional objects and advantages of the present invention will be apparent from the following detailed description of a preferred embodiment, which proceeds with reference to the accompanying drawings.

BRIEF DESCRIPTION OF DRAWINGS

FIG. 4 is an enlarged top view of the conveyor belt shown in FIG. 1.

DETAILED DESCRIPTION OF A PREFERRED EMBODIMENT

Figure 1:
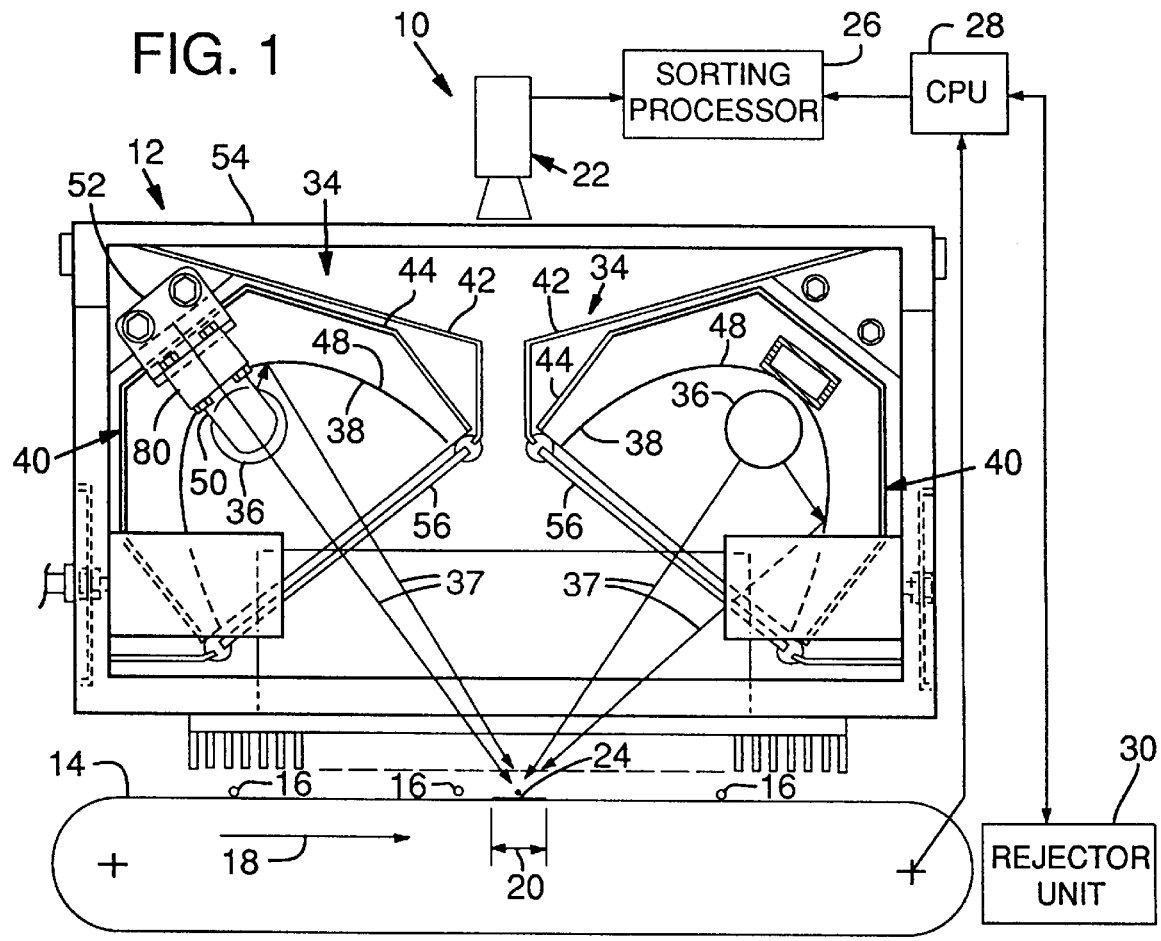
FIG. 1 is a diagram showing a side elevation view of an illustrative optical inspection system operable in accordance with the present invention.
Figure 2:
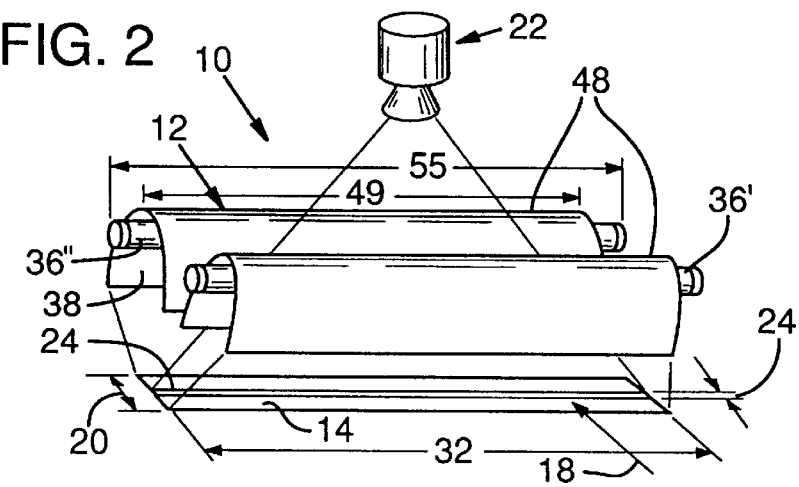
FIG. 2 is an isometric view of the illumination system shown in FIG. 1, with parts removed for clarity.

FIGS. 1 and 2 show an illustrative automated optical inspection system 10 suitable for carrying out a method according to the invention. Inspection system 10 may be of the on-belt specimen inspection and sorting type described in U.S. Pat. Nos. 4,738,175 to Little et al. for a DEFECT DETECTION SYSTEM and 5,085,325 to Jones et al. for a COLOR SORTING SYSTEM AND METHOD. Both of these patents are assigned to the assignee of this patent application. Although inspection system 10 is shown as an on-belt inspection system, the methods of the invention can also be carried out with the use off-belt inspection systems such as that described in U.S. Pat. No. 5,305,894 granted to McGarvey for a CENTER SHOT SORTING SYSTEM AND METHOD, which is assigned to the assignee of this patent application.

Inspection system 10 employs an illumination system 12 and an endless conveyor belt 14 having a width of about 1.2 meters (48 inches) to move potato pieces 16 as quickly as 2.5–3.0 meters per second (500–600 feet per minute) in a direction 18 across an illumination area 20. It would be typical for many products that most of the pieces would have at least some peel-bearing surface portions 108 (FIG. 4).

A high-resolution line scan video camera 22 having a one-dimensional pixel array scans potato pieces 16 as they pass through a scanning area 24 within illumination area 20. Camera 22 uses a lens having a focal length that images the width across belt 14 of image scanning area 24 onto the full width of its pixel array. Camera 22 is compatible with other system parameters such as belt speed and illumination intensity and provides 2048 pixels per scan; it thus resolves a distance of about 0.6 mm (about 0.023 inch) across belt 14 into one pixel. The camera completes a scan once each millisecond. Camera 22 may include more than one unit; e.g., it may be two lower-resolution (1024 pixel) cameras mounted side by side. A camera that can be used for this purpose is a SRC Black and White Infrared 1024 Pixel Camera made by SRC Vision, Inc., P.O. Box 1666, Medford, Oregon, 95401, which is the assignee of this patent application.

Camera 22 samples the intensity of light reflected by potato pieces 16 and assigns a brightness value for each pixel ("pixel value"). The intensity of each pixel value is a function of the spectral power distribution of the source of illumination, the spectral response of the location from which the camera is receiving light energy at the time the pixel value is detected ("pixel location"), and the spectral response of camera 22. A sorting data processor 26 processes image data generated by video camera 22 and arranges these data in image frames containing a user selectable number of scan lines.

A central data processor unit 28 linked with sorting data processor 26, conveyor belt 14, and a rejector unit 30 synchronizes the timing of the position of potato pieces 16 to the operation of rejector unit 30. Rejector unit 30 sorts and removes specimens 16 rejected by sorting data processor 26. With respect to potato piece samples 16, data processor 26 rejects those pieces that have an above threshold number of poorly reflective pixels. Poor reflectivity indicates the presence of a potato defect such as an "eye," potato green flesh, or potato rot.

Illumination system 12 includes multiple, preferably two, light source assemblies 34 positioned to project near infrared light across the width of belt 14 at scanning area 24 in illumination area 20. Each light source assembly 34 includes one of two nonfluorescing rare gas discharge lamps 36 for emitting respective high-intensity light rays 37 of wavelengths that reflect off an inner light-reflecting surface 38 of a shroud-like reflector structure 40 and are directed toward illumination area 20. Light rays 37 have a spectral power distribution shown in FIG. 3. Lamps 36 are cooled by forced air.

Each of lamps 36 contains a rare or noble gas or a mixture of rare gases. Each rare gas and each mixture of rare gases emits select wavelengths of high-intensity illumination when ionized at the breakdown voltage. Lamps 36 emit light rays 37 with an intensity approximately two to three or more times that of conventional fluorescent sources. The intensity of the light rays reflected from potato pieces 16 depends upon the distance between a respective one of lamps 36 and potato pieces 16. Both argon and xenon are preferred gasses for use in the present invention. Lamps 36 are filled to a pressure of approximately 665 Pa (Newtons per square meter) (approximately 5 Torr). A preferred distance between each of lamps 36, and between lamps 36 and potato pieces 16 is 15.24 cm (6 inches).

Reflector structure 40, which fits within and is supported by an outer covering 42 of each light source assembly 34, includes a housing 44 and a preferably hemi-elliptical reflector 48 secured within housing 44. Each of lamps 36 may be held in place by, for example, a pair of tube sockets 50 that are supported by a light source support member 52 connected to frame 54. The length 55 of each of lamps 36 is generally a function of and typically greater than length 32 of scanning area 24.

Each of lamps 36 is positioned within rectangular frame 54 so that it lies in a direction generally perpendicular to conveyor belt travel direction 18 to illuminate potato pieces 16 as they are scanned by video camera 22. Light rays 37 propagate directly toward illumination area 20. Light rays 37 also propagate toward and reflect from light-reflecting surface 38 of hemi-elliptical reflector 48 toward illumination area 20. Hemi-elliptical reflectors 48 have lengths 74 that are about equal to length 32 of scanning area 24 and about equal to or shorter than length 55 of lamps 36. Because reflectors 48 are of hemi-elliptical shape, reflectors 48 produce a line focus of light rays 37 that strike illumination area 20 and scanning area 24 on conveyor belt 14.

Lamps 36 also typically have a smaller diameter than the diameters of conventional broad-spectrum fluorescent tubes. When used with hemi-elliptical reflectors, smaller diameter lamps more closely approximate a line source of illumination than larger diameter lamps. Line sources are more efficient than diffuse sources of illumination.

Preferably, an optically transmissive protective covering 56 encloses reflector structure 40 to protect potato pieces 16 from debris falling from a broken lamp 36. Also, hemi-elliptical reflector 48 supports a preformed aluminum substrate that carries on its inner surface 38 a light-reflective coating such as, for example, the "BV2 coating" having 89 to 93 percent reflectivity, which is produced by Optical Coating Labs, Inc. of Santa Rosa, Calif.

Lamps 36 are described in great detail in U.S. Pat. No. 5,440,127 to Squyres for METHOD AND APPARATUS FOR ILLUMINATING TARGET SPECIMENS IN INSPECTION SYSTEMS, which is assigned to the assignee of this patent application.

Each of lamps 36 plugs into tube socket 50 of lamp fixture 80, which is designed to support such a lamp 36 and to supply electrical current to it.

Figure 3:
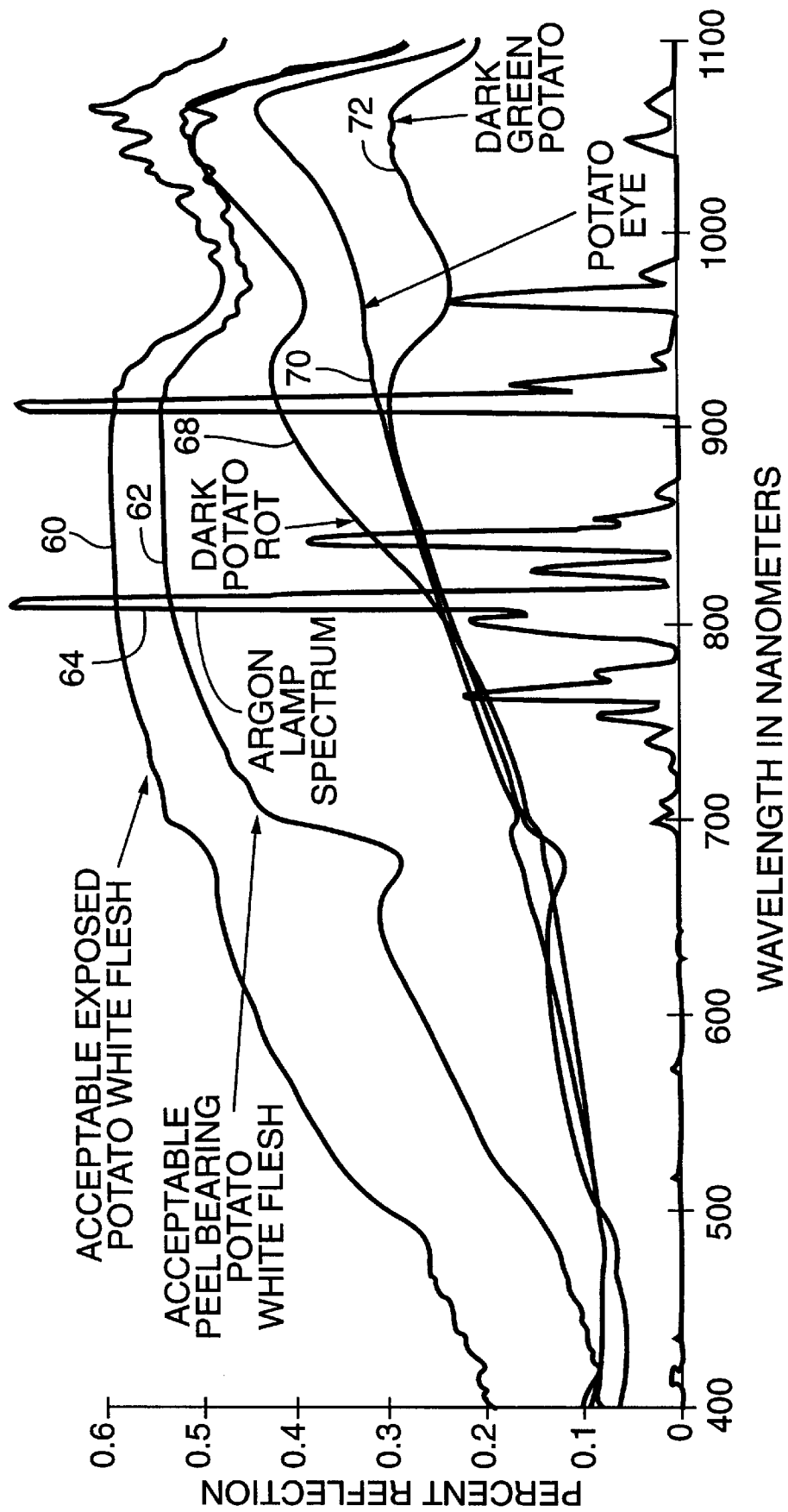
FIG. 3 is a graph showing the comparative relationships among reflectivities of peeled acceptable potato white flesh; peel-bearing acceptable potato white flesh, and peeled defective potato flesh in relation to the spectral energy distribution of an argon gas discharge lamp over the 400–1100 nm wavelength range of FIG. 3.

FIG. 3 graphically shows a set of reflectivity measurements of acceptable exposed potato white flesh (curve 60), acceptable peel-bearing potato white flesh (curve 62), dark potato rot (curve 68), potato eye (curve 70), and dark green potato (curve 72) over a range of wavelengths of visible and infrared light. An argon lamp light energy spectrum (curve 64) is shown superimposed on curves 60, 62, 68, 70, and 72. Visible light has wavelengths ranging from about 400 nm to about 710 nm; whereas near infrared light has wavelengths ranging from about 750 nm to about 1100 nm.

FIG. 3 shows that it is possible to distinguish acceptable exposed or peel-bearing potato white flesh from defective exposed or peel-bearing potato flesh by using the light from an argon lamp. In the spectral range containing most of the argon lamp light energy, curves 60 and 62 for acceptable exposed and peel-bearing potato white flesh are quite close to each other. In addition, curves 60 and 62 are well separated from curves 68, 70 and 72 showing the reflectivities of potato flesh with defects.

In addition, the proximity of curve 60 to curve 62 in the infrared region is a manifestation of the increased transmissivity of potato peel in infrared light as opposed to visible light. This transmissivity permits the detection of peel covered defects. Infrared light rays 74 penetrate through the potato peel and into the potato flesh, where they are reflected at varying depths. If good white potato flesh lies underneath the potato peel, a relatively strong return is reflected back through the peel toward camera 22. A peel covered defect, however, will be less reflective of light rays 74 and will appear as a dark spot to camera 22, thereby permitting detection and removal.

FIGS. 1, 2, and 4 show a preferred embodiment of a potato piece sorting system. Potato pieces 16 are continuously introduced onto the surface of conveyor belt 14, which is preferably white. Because they are quite slippery, potato pieces 16 typically slide past one another onto belt 14 and therefore do not rest on top of or cover a portion of one another. Potato pieces 16 have exposed portions 106 and peel-bearing portions 108. One of potato pieces 16 bears a defect 110.

Camera 22 repeatedly scans transversely across the width of conveyor belt 14 gathering a sequence of light intensity samples, also referred to as "pixels," each one corresponding to a unique scan position across belt 14. A multiplicity of pixel locations 111 (shown at a greatly enlarged scale for ease of description) are divided into pixel sets 112, 114, 116, and 118, each of which corresponds to a separate camera scan across belt 14. Because belt 14 moves in direction 18 as camera 22 is scanning repeatedly, camera 22 views an incrementally changed portion of belt 14 with each new scan. Therefore, pixel set 118 is detected prior to pixel set 116, which is detected prior to pixel set 114, which is detected prior to pixel set 112.

Pixel values corresponding to pixel locations 111 on belt 14 will be higher than pixel values corresponding to locations 111 on acceptable potato flesh, which, in turn, will be higher than values corresponding to locations 111 on defective potato flesh 110. Therefore, only defective portion 110 of potato pieces 16 need be identified. A light intensity threshold is set to distinguish the pixel values corresponding to the reflectivity of peel-bearing potato from the pixel values corresponding to the reflectivity of defective potato flesh. In addition, a number-of-pixels threshold is set whereby if consecutive pixel values from locations 111 in a single scan numbering in excess of this threshold are each below the light intensity threshold, a defective area will be recognized by data processor 26.

Each pixel value is first compared with the light intensity threshold. When a first pixel value from pixel set 112, for example, is below the light intensity threshold, a count is begun of all subsequent consecutive pixel values that are below the light intensity threshold. If this count exceeds the number-of-pixels threshold, a rejection is declared by sorting data processor 26 and central data processor 28 commands rejector unit 30 to remove the piece 16 bearing the defect.

Sorting data processor 26 and central data processor 28 are typically devices that comprise a microprocessor such as an Intel 80386® and supporting circuitry. These data processors are widely available. One popular and widely used variety of this sort of data processor is an Advanced Technology Processor Model 3220 sold by TMT Corp. of Houston, Tex. Rejector unit 30 most typically is comprised of a row of closely spaced air blowers or "puffers" placed transversely to the direction 18 of potato piece 16 movement and displaced slightly in direction 18 from the end of belt 14. These puffers are controlled so that when a defective potato piece 16 is lofted from the end of belt 14, a puff of air knocks it into a "defect bin." This kind of rejector unit is shown in earlier referenced US. Pat. No. 5,305,894.

Alternatively, data processor 26 could compare pixel values from neighboring locations 111 in consecutive sets and use a two-dimensional criteria for declaring a defective area. For example, if pixels from neighboring locations in pixel set 118 and pixel set 116 failed the light intensity threshold, the number of such pixel values from pixel set 118 and pixel set 116 could be computed and compared to a alternative number-of-pixels threshold to declare a defective area.

Although lamps 36 are preferred sources of illumination, other sources of illumination in the near infrared can also be effective. Gas discharge lamps with other gas mixtures could be used. Instead of or in addition to gas discharge lamps, the illumination could be provided by one or more lasers. Gas lasers produce high-intensity emission at about 904 nm and can be tuned to produce emissions at other wavelengths in the near infrared by varying the trapping levels with additions of suitable phosphors. Such lasers would be especially useful with a camera 22 that used a silicon detector. Nd:YAG (neodymium:yttrium-aluminum-garnet) lasers produce high-intensity emission at about 1064 nm.

The spectral energy distribution of the detected illumination may be different from that of lamps 36. A silicon detector, which is preferably used in camera 22, has maximum response at about 750 nm and substantially reduced response at about 400 nm and about 1100 nm.

It will be obvious to those having skill in the art that many changes may be made to the above-described details of the preferred embodiment of the invention without departing from the underlying principles thereof. For example, illumination system 12 may also comprise multiple video cameras 22, a single light source 36 and hemi-elliptical reflector 48, and light source or sources 36 at various distances and angles from conveyor belt 14. The scope of the present invention should, therefore, be determined only by the following claims.

I claim:

1. In an automated optical inspection process, a method of detecting in potatoes having at least partly peel-covered flesh surfaces a presence of flesh surface regions in defective condition hidden by peel material, the potatoes included in a random mixture of peel-bearing acceptable and peel-bearing defective potatoes, comprising:

illuminating the mixture with near infrared light, the potato flesh surfaces including flesh surface regions in sound condition and flesh surface regions in defective condition that are, respectively, more reflective and less reflective of the near infrared light, and the peel material being at least partly transparent to the near infrared light so that a mere presence of peel material is not indicative of a defect;

detecting reflections of near infrared light from the mixture; and analyzing the detected reflections of near infrared light to identify peel-covered flesh surface regions in defective condition as those of peel-bearing defective potatoes in the mixture.

2. The method of claim 1, further comprising removing from the mixture potatoes identified as having peel-covered flesh surface regions in defective condition.

3. The method of claim 1, in which the analyzing of the detected reflections includes identifying reflections that have less than a predetermined intensity.

4. The method of claim 1, in which the near infrared light is emitted by a laser, an argon lamp, a xenon lamp, or a broad band lamp.

5. The method of claim 1, in which the detecting of reflections of near infrared light is performed by a device that detects substantially exclusively infrared light.

6. The method of claim 1, in which a conveyor belt having a length transports the mixture of potatoes for optical inspection and in which the detecting of reflections of near infrared light is performed by a camera that repeatedly scans transversely to the length of the conveyor belt to form a sequence of sets of pixel values, each set of pixel values corresponding to a separate camera scan.

7. The method of claims 6, in which the identifying peel-covered flesh surface regions in defective condition includes examining the sets of pixel values.

8. The method of claim 7, in which the identifying peel-covered flesh surface regions in defective condition includes examining each set of pixel values separately.

9. The method of claim 7, in which the identifying peel-covered flesh surface regions in defective condition includes examining each set of pixel values in conjunction with its neighboring sets of pixel values.

\* \* \* \* \*